United States Patent
Stefan

(10) Patent No.: US 9,566,081 B2
(45) Date of Patent: Feb. 14, 2017

(54) ACTUATION GRIP FOR A MICROSURGICAL INSTRUMENT, AND MICROSURGICAL INSTRUMENT

(71) Applicant: Karl Storz GmbH & Co. KG, Tuttlingen (DE)

(72) Inventor: Jochen Stefan, Wald (DE)

(73) Assignee: Karl Storz GmbH & Co. KG, Tuttlingen (DE)

( * ) Notice: Subject to any disclaimer, the term of this patent is extended or adjusted under 35 U.S.C. 154(b) by 247 days.

(21) Appl. No.: 14/062,416

(22) Filed: Oct. 24, 2013

(65) Prior Publication Data

US 2014/0121692 A1    May 1, 2014

(30) Foreign Application Priority Data

Oct. 26, 2012   (DE) .................. 10 2012 110 260

(51) Int. Cl.
| | | |
|---|---|---|
| *A61B 17/00* | (2006.01) | |
| *A61B 17/29* | (2006.01) | |

(Continued)

(52) U.S. Cl.
CPC ....... *A61B 17/2909* (2013.01); *A61B 17/2812* (2013.01); *A61B 17/3201* (2013.01);
(Continued)

(58) Field of Classification Search
CPC ............ A61B 17/2812; A61B 17/2909; A61B 17/3201; A61B 2017/0046; A61B 2017/2919; A61B 2017/292; A61B 2017/305; A61B 17/1285; A61B 17/29; A61B 17/083; A61B 2017/2916; A61B 2017/1107; A61F 9/00736; A61F 2002/9517

(Continued)

(56) References Cited

U.S. PATENT DOCUMENTS

| | | | | |
|---|---|---|---|---|
| 5,020,519 A | * | 6/1991 | Hayes ................. | A61B 17/025 600/226 |
| 5,192,298 A | * | 3/1993 | Smith .................... | A61B 17/29 30/251 |

(Continued)

FOREIGN PATENT DOCUMENTS

| | | |
|---|---|---|
| DE | 69532918 T2 | 9/2004 |
| DE | 102010013916 A1 | 10/2011 |
| EP | 1201193 B1 | 12/2008 |

*Primary Examiner* — Katherine M Shi
*Assistant Examiner* — Mohamed Gabr
(74) *Attorney, Agent, or Firm* — Whitmyer IP Group LLC

(57) ABSTRACT

An actuation grip for a microsurgical instrument, with an inner shaft, which is surrounded coaxially and cylindrically by an outer shaft, wherein the shafts are axially movable relative to each other. Two pivotable grip parts, each with two ends, are coupled pivotably at a proximal end of the actuation grip. On each grip part, a first lever is articulated rotatably via an attachment point between the ends of the grip part, wherein the two first levers are coupled rotatably to each other at an intersection point between their ends. The first levers are each connected rotatably to a second lever at their ends directed away from the grip parts, such that the first levers form, with the second levers, a double scissor hinge which serves to move the two shafts axially relative to each other, in order to use this movement to actuate a surgical tool.

20 Claims, 3 Drawing Sheets

(51) Int. Cl.
  *A61B 17/28* (2006.01)
  *A61B 17/3201* (2006.01)
  *A61B 17/30* (2006.01)

(52) U.S. Cl.
  CPC . *A61B 2017/0046* (2013.01); *A61B 2017/292* (2013.01); *A61B 2017/2919* (2013.01); *A61B 2017/305* (2013.01)

(58) Field of Classification Search
  USPC ............................................................ 606/205
  See application file for complete search history.

(56) References Cited

U.S. PATENT DOCUMENTS

| | | | | |
|---|---|---|---|---|
| 5,201,743 A * | 4/1993 | Haber | ................ | A61B 17/0469 606/146 |
| 5,251,638 A * | 10/1993 | Cottone, Jr. | ........... | A61B 10/06 600/564 |
| 5,275,613 A * | 1/1994 | Haber | .................... | A61B 17/29 606/139 |
| 5,282,806 A * | 2/1994 | Haber | .................... | A61B 17/29 606/139 |
| 5,308,357 A * | 5/1994 | Lichtman | ........... | A61B 17/2909 606/205 |
| 5,478,351 A * | 12/1995 | Meade | .................... | A61B 17/29 606/174 |
| 5,501,698 A * | 3/1996 | Roth | .................... | A61B 17/1285 606/174 |
| 5,507,773 A * | 4/1996 | Huitema | .......... | A61B 17/07207 600/564 |
| 5,519,920 A * | 5/1996 | Runge | .................... | E05D 3/022 16/221 |
| 5,690,673 A * | 11/1997 | Koscher | ............. | A61B 17/2909 600/564 |
| 5,720,756 A * | 2/1998 | Green | ................ | A61B 17/1285 227/901 |
| 5,810,877 A * | 9/1998 | Roth et al. | .................... | 606/205 |
| 5,868,761 A * | 2/1999 | Nicholas | ............ | A61B 17/1285 606/139 |
| 5,891,140 A * | 4/1999 | Ginn | .................... | A61B 18/1445 606/45 |
| 5,893,873 A * | 4/1999 | Rader | ................ | A61B 17/2909 606/205 |
| 5,928,263 A * | 7/1999 | Hoogeboom | ...... | A61B 17/2909 606/180 |
| 5,954,746 A * | 9/1999 | Holthaus | .......... | A61B 17/32009 606/169 |
| 6,024,748 A * | 2/2000 | Manzo | .................... | A61B 17/11 206/340 |
| 6,083,234 A * | 7/2000 | Nicholas | ................ | A61B 17/11 606/153 |
| 6,322,578 B1 * | 11/2001 | Houle | ................ | A61B 17/2909 600/564 |
| 6,391,039 B1 * | 5/2002 | Nicholas | ................ | A61B 17/11 606/153 |
| 6,533,797 B1 * | 3/2003 | Stone | .................. | A61B 17/2909 606/1 |
| 6,641,595 B1 * | 11/2003 | Moran | ............... | A61B 17/2909 606/205 |
| 6,769,594 B2 * | 8/2004 | Orban, III | .......... | A61B 17/0644 227/176.1 |
| 7,195,142 B2 * | 3/2007 | Orban, III | ............. | A61B 17/11 227/176.1 |
| 7,204,843 B2 * | 4/2007 | Milliman | ............... | A61B 17/11 606/153 |
| 7,223,273 B2 * | 5/2007 | Manzo | ................... | A61B 17/11 227/179.1 |
| 7,556,637 B2 * | 7/2009 | Dausch | .............. | A61B 17/1608 606/208 |
| 7,578,828 B2 * | 8/2009 | Gittings | ................. | A61B 17/11 606/153 |
| 8,905,937 B2 * | 12/2014 | Ellingwood | ........... | A61B 5/053 600/481 |
| 8,979,879 B2 * | 3/2015 | Terao | ................... | A61F 9/00754 606/170 |
| 9,333,103 B2 * | 5/2016 | Costello | ................... | A61F 2/962 |
| 2001/0056286 A1 * | 12/2001 | Etter | ................... | A61B 17/2909 606/205 |
| 2004/0097971 A1 * | 5/2004 | Hughett | ............... | A61B 17/068 606/142 |
| 2005/0165429 A1 * | 7/2005 | Douglas | ................. | A61B 17/08 606/157 |
| 2006/0079933 A1 * | 4/2006 | Hushka | ............. | A61B 17/2909 606/205 |
| 2007/0198002 A1 * | 8/2007 | Melsheimer | ......... | A61B 17/221 606/1 |
| 2011/0022054 A1 * | 1/2011 | DiStefano | .............. | A61B 17/04 606/103 |
| 2011/0245864 A1 * | 10/2011 | Besse | ..................... | A61B 17/29 606/205 |
| 2012/0179260 A1 * | 7/2012 | Nottingham | ......... | A61B 17/025 623/17.16 |
| 2013/0116707 A1 * | 5/2013 | Seibold | .................. | A61B 17/29 606/130 |
| 2014/0330308 A1 * | 11/2014 | Hart | ....................... | A61B 17/29 606/207 |
| 2014/0379024 A1 * | 12/2014 | Schaller | .................. | A61B 17/29 606/210 |
| 2015/0025571 A1 * | 1/2015 | Suzuki | ............... | A61B 17/2909 606/205 |
| 2015/0059535 A1 * | 3/2015 | Ford, Jr. | .................. | B25B 5/006 81/116 |
| 2016/0008936 A1 * | 1/2016 | McIntosh | ............... | B23Q 3/062 269/54.1 |
| 2016/0113637 A1 * | 4/2016 | Abri | ................. | A61B 17/00234 606/1 |

\* cited by examiner

ACTUATION GRIP FOR A MICROSURGICAL INSTRUMENT, AND MICROSURGICAL INSTRUMENT

FIELD OF THE INVENTION

The invention relates to a microsurgical instrument for minimally invasive surgery and to an actuation grip for same.

BACKGROUND OF THE INVENTION

Microsurgical instruments for minimally invasive surgery have to meet particular demands specifically as regards a high degree of precision and the ability to control them ergonomically (i.e. with optimized control forces and kinematics) and using one hand. Minimally invasive surgery is increasingly being used for interventions which hitherto required opening the body of the patient at the appropriate locations, since with this surgery it is possible largely to avoid the negative effects of trauma.

The prior art discloses the use of microsurgical instruments in microsurgery, e.g. in endoscopic cardiovascular surgery. These microsurgical instruments comprise a tool which is arranged distally on a guide shank and which is in most cases composed of two jaws, of which at least one is movable, and an actuation grip which is mounted proximally on the guide shank and which is operated by the surgeon. The microsurgical instrument, along with its actuation grip, can be designed such that it can be actuated ergonomically by the surgeon; the control displacements performed on the actuation grip by the surgeon should be translated into the shortest possible working displacements of the tool. Such an actuation grip is often designed as a "forceps handle", i.e. the surgeon holds and actuates the actuation grip like forceps or scissors.

DE 695 32 918 T2 discloses a microsurgical instrument having a known one with a forceps grip. It has an outer shank and an inner shank, which are movable relative to each other. A surgical tool, which can be controlled by the relative movement of the shanks, is mounted on a distal end. An adjustment member with two symmetrical levers is arranged at the proximal end of the outer shank for the purpose of manipulating the tool. At a pivot point, which lies closer to the proximal end than to the distal end of the levers, the levers are coupled to one of the two shanks, the outer shank or the inner shank, wherein the proximal ends of the levers are connected pivotably to the respective other shank. One end of an elongate connection member is mounted pivotably at the pivot point of the levers, wherein the respective other ends of the connection members of the two levers are mounted rotatably on a common pin on one of the two shanks. During a pivoting movement of the levers, this pin moves in an axial direction, as a result of which the tool can be actuated, i.e. it is a simple scissor hinge which is controlled directly by the levers. In a lever excursion by a fixed amount, a mechanism of this kind for converting a pivoting movement of the levers into an axial movement leads to a much greater axial excursion when the levers are positioned closely than when the levers are positioned wide open, and the maximum possible transmission ratio is greatly limited.

DE 10 2010 013 916 A1 also discloses such an instrument which is actuated by means of a forceps grip which is present at the proximal end of a hollow shank, and at the distal end it has a surgical tool which is actuated by means of the grip via an actuating rod that is mounted so as to be axially movable in the shank. The levers are operatively connected to the actuation rod via a pin-and-slot control system, at the proximal end of which arms are arranged which protrude outward at right angles and at whose ends control pins are present. These are guided in guide tracks or guide grooves in the grip parts of the handle, wherein the guide tracks are at an acute angle with respect to the longitudinal axis of the hollow shank in a rest position and, during a pivoting movement of the levers, convert this movement into an axial movement of the actuation rod. This mechanism too has a not entirely homogeneous transmission ratio, which reduces the control precision. In addition, the maximum possible transmission ratio is relatively small, and the mechanism is expensive to produce and susceptible to production fluctuations. The partially open mechanism is susceptible to contamination and, during an operation, can become jammed on a trocar sleeve or an incision opening, which greatly restricts the freedom of movement of the operating surgeon.

SUMMARY OF THE INVENTION

Proceeding from this prior art, the object of the present invention is to provide a medical instrument of this kind with an actuation grip which offers an improved transmission ratio and more homogeneous transmission across the complete pivot range of the grip parts and which as far as possible has no parts of its mechanism lying open and has slight play.

This object is achieved by an actuation grip having the claimed features.

Furthermore, there is the object of making available a microsurgical instrument which allows the operating surgeon to execute extremely small movements of a surgical instrument with low force input and maximum control.

Preferred embodiments are described in each of the dependent claims.

A first embodiment of the actuation grip according to the invention for a microsurgical instrument has at least one inner shank, which is surrounded coaxially and cylindrically by an outer shank, wherein the shanks are axially movable relative to each other. Two pivotable grip parts, each with two ends, are coupled pivotably at a proximal end of the actuation grip and form an ergonomic "forceps handle". The inner shank can be hollow at least in some areas. The "proximal end" is here understood as the end of the handle or instrument lying in the hand of the surgeon. Accordingly, "distal end" signifies the end lying opposite the proximal end and arranged away from the surgeon and toward the patient.

On each grip part, a first lever having substantially an S-shape is articulated rotatably via an attachment point between the ends of the grip part. The two first levers have, in each case at an intersection point between their ends, a bore in which an axial pin is arranged which couples the two first levers rotatably to each other, wherein the axial pin is mounted movably in an oblong hole in at least one of the two shanks and is thus guided on the main axis of the instrument. The intersection point is a common intersection point, wherein "in each case" is intended to signify that there is a bore present in both of the first levers, and the two bores are arranged congruently for insertion of the axial pin.

The first levers, at their ends directed away from the grip parts, are each connected rotatably to at least one second lever, such that the first levers form, with the second levers, a double scissor hinge. Moreover, the second levers, at their ends directed away from the first levers, are mounted rotatably on a common guide pin, wherein the guide pin is secured in opposite recesses in the shank wall of a shank which is movable and serves for the actuation of the tool. The S-shaped first levers are here advantageously designed such that they have a relatively long portion between the attachment point on the grip parts and the intersection point and have a relatively short portion between the intersection point and the rotation point where the second levers are attached, wherein the curvature of the second arch of the "S", in the area between the intersection point and the rotation point where the second levers are connected in an articulated manner to the grip parts, also has a much smaller radius of curvature. The narrower radius of curvature of the "S" of the first levers is also described by the second levers which, for instance, can have the shape of a very flat "U".

The double scissor hinge serves to ensure that a pivoting movement of the grip parts, which is transmitted to the double scissor hinge by means of the first levers, is converted into an axial movement and transmitted to the shanks, as a result of which the latter can be moved axially relative to each other.

Compared to the known pin-and-slot control, the double scissor hinge has the advantage that much greater transmission ratios can be achieved. This means that, by using the actuation grip according to the invention, an operating surgeon is able to control very precisely the movements of a surgical instrument. In addition, the high transmission ratio that can be achieved helps to keep the control forces low and thus allows the surgeon to work in a way that does not cause fatigue, which also helps to avoid operating errors. Moreover, an actuation grip according to the invention can also be produced more efficiently than, for example, an actuation grip equipped with the known pin-and-slot control system, since manufacturing tolerances in the pin-and-slot control system have a much greater influence on the transmission ratio, because very small irregularities on the running tracks of the pins lead to a spontaneous change of the transmission ratio and to increased friction. By contrast, the actuation grip according to the invention can be produced with relatively wide tolerances, since the transmission ratio is determined by the ratio of the lengths of the levers and by their shape, and not by surface properties.

According to a preferred embodiment, the guide pin can be secured in opposite recesses of a shank wall of the inner shank.

This embodiment is distinguished by a compact structure. Moreover, by securing the guide pin in the inner shank, it is possible for the outer shank to be designed without an opening in this area, which makes it easier to keep an actuation grip of this kind sterile, because the hollow spaces in the interior of the outer shank are as it were inaccessible at this location.

In a preferred embodiment, at the intersection point where the two first levers cross each other, the axial pin can extend with both ends beyond the congruent bores of the first levers, wherein the axial pin is guided at both ends thereof in a respective oblong hole present in the inner or outer shank. In addition, guide rollers, which roll in the oblong hole, can be arranged on the ends of the axial pin.

The guiding of the axial pin in the oblong holes of the inner or outer shank has the effect that, upon actuation by the operating surgeon, the first levers or the grip parts cannot be moved too much in a direction that does not correspond to the predetermined pivoting direction. In particular, the guiding of the axial pin reduces a degree of freedom of rotation of the first levers or grip parts about the longitudinal axis of the shanks, thereby permitting a very precise control of the actuation displacement and a high-quality actuation experience. If no guide rollers are used, i.e. the axial pin slides in the oblong hole, a compromise always has to be found between angular play about the longitudinal axis and a still acceptable actuation force, whereas the use of guide rollers leads to a minimal angular play and at the same time to low actuation forces. The guide rollers can be designed, for example, as guide rollers which are mounted on roller bearings or slide bearings and which are operable with or without lubricant.

According to a further embodiment, on a circumference on which the oblong holes are also present, the inner shank has, offset by 90° with respect to the oblong holes, an insert slit for the first levers.

The insert slit is therefore a continuous radial groove, i.e. open at both sides, which extends along the longitudinal axis of the shank and which is connected to the oblong holes. The first levers are introduced through or into the insert slit, and the second levers are also located partially therein, wherein the second levers, for the purpose of a compact structure, do not protrude radially from the insert slit or from the outer contour of the inner shank.

Moreover, the actuation grip according to the invention can have a change-over device for microsurgical instruments, wherein a quick-change device is advantageous since in this way, for example during an ongoing operation, several different microsurgical instruments can be controlled with the same actuation grip.

Furthermore, one of the first levers can be composed of two identical first lever halves which are arranged in parallel planes and are spaced apart from each other along the axial pin, wherein the other first lever, which is in one part, is received between the two lever halves. For this purpose, the two lever halves can have a smaller thickness than a one-part lever. At its end directed away from the grip part, the one-part first lever is in turn received by a second lever, which is composed of two identical second lever halves which are arranged in parallel and are spaced apart from each other along the guide pin.

This embodiment has the effect that the introduction of force from the grip parts to the double scissor hinge can ideally take place centrally and without tilting of the first or second levers, which contributes to precise controllability and little play.

The first levers can be longer than the second levers, wherein the length ratio advantageously lies in a range between 1 to 15 and 1 to 3, and a range between 1 to 12 and 1 to 6 is particularly advantageous. The transmission ratio of the kinematics can be adjusted by means of the length ratio of the first levers to the second levers and the position of the intersection point of the first levers. A high transmission ratio is sought in order to ensure that even very small movements of a surgical tool can be controlled by comparatively rough manual movements by means of the actuation grip, wherein the attainable force available for actuation of the surgical tool is also increased.

In an alternative embodiment, at least one grip part can be locked, by means of a locking device, in a predetermined angle position with respect to a longitudinal axis of the shanks. The locking device can be any of the locking devices known to a person skilled in the art, such as corresponding clips and prongs, a latch mechanism, or a ratchet device, wherein a latch mechanism also allows the grip part to be locked in angle positions that are not its end positions. A locking possibility is helpful to an operating surgeon, for example if tissue parts are to be clamped during an operation.

Alternatively or in addition, the actuation grip can also be designed with an axial spring element in one of the shanks, in order to transmit force to the respective other shank. With an axial spring element of this kind, it is possible for the actuation grip to "spring back" at any time to its rest position when the grip parts are released. It is also possible in principle to use another spring element that is suitable for applying an axially directed force to the two shanks and/or for moving the grip parts outward to their rest position, which spring element can be, for example, a leaf spring arranged at the proximal end and operatively coupled to the grip parts.

Moreover, the double scissor hinge can be present entirely within an outer contour of the inner shank, as a result of which the mechanism is protected from harmful effects and contamination. Moreover, this increases the freedom of movement of the operating surgeon since there is no open mechanism, for example the pin-and-slot control system or the known open single scissor hinges, that can become caught on trocar sleeves or incision openings in the patient's body, and therefore movements that were hitherto not possible are permitted.

A first embodiment of a microsurgical instrument for minimally invasive surgery has at least one hollow shank and an actuation device movable axially thereto, wherein, at a proximal end, there is an actuation grip according to the invention coupled by means of a change-over device for actuation grips, and, at a distal end, there is a surgical tool. The surgical tool can be actuated by the actuation device, wherein the actuation grip is operatively coupled to the actuation device.

By means of the microsurgical instrument according to the invention, very small movements of a surgical tool can be performed with low force input and a high degree of control. By using an actuation grip according to the invention with a high transmission ratio, rough manual movements can also be converted to very fine movements of the surgical tool.

The surgical tool can also be in the form of scissors, forceps, a gripper or a pincer, it being possible for all surgical tools to be used that are known to a person skilled in the art and that can be controlled by a described axial movement.

These and further advantages are set forth in the following description, in which reference is made to the accompanying figures. Items, or parts of items, which are substantially the same or similar can be provided with the same reference signs. The figures are only schematic representations of illustrative embodiments of the invention.

DETAILED DESCRIPTION OF THE INVENTION

Figure 1:
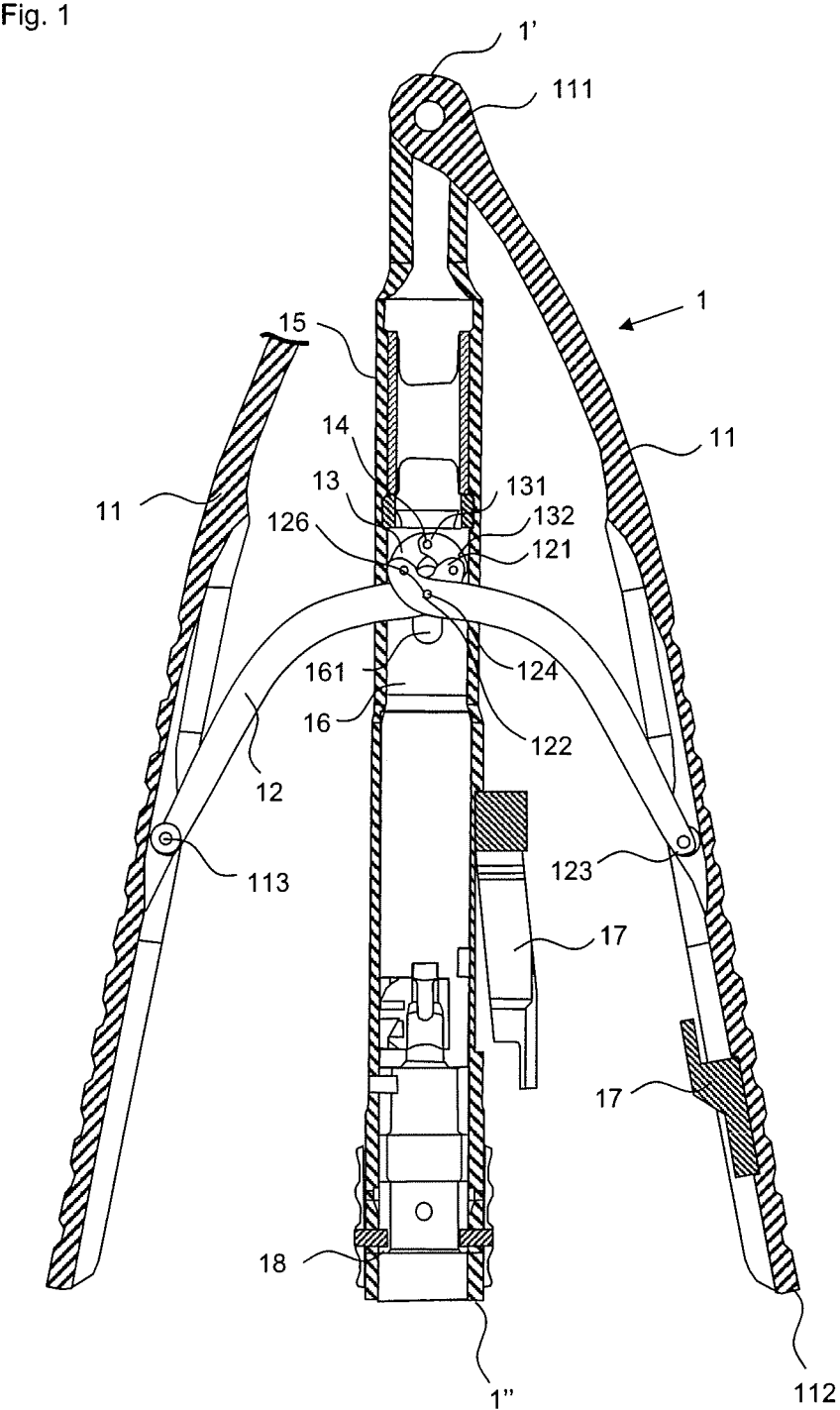
FIG. 1 shows a longitudinal section through an actuation grip.

An actuation grip 1 according to the invention has two grip parts 11, which are coupled rotatably to the outer shank 15 at a common point located at their proximal end 111, as is shown in FIG. 1, the latter showing a longitudinal section in which the sectional plane contains the longitudinal axis of the shanks 15, 16. According to the invention, both grip parts 11 extend as far as the proximal end 1' of the actuation grip 1, wherein one grip part 11 is shown sectioned on account of the position of the sectional plane. At an attachment point 113 located between the proximal end 111 and the distal end 112 of the grip parts 11, the latter are each rotatably coupled to a first long S-shaped lever 12, such that, with two grip parts 11, two first levers 12 are present which, at their ends 123 directed toward the grip parts 11, are coupled rotatably thereto. Between their ends 123 directed toward the grip parts 11 and their ends 121 directed away from the grip parts 11, the first levers 12 have an intersection point 122 at which through-bores 126, formed in both first levers 12, lie congruently over each other, and wherein an axial pin 124, which connects the two first levers 12 in an articulated manner, is inserted through the through-bores 126. At their ends 121 directed away from the grip parts 11, the first levers 12 are each connected to the second levers 13, and the second levers 13 are in turn connected to each other at their ends 131, which results in a double scissor hinge. The connection of the second levers 13, at their ends 131 directed away from the first levers 12, is effected by means of a guide pin 14.

For the transmission ratio that can be achieved by the double scissor hinge, important factors are the length ratios of the first levers 12 to the second levers 13 and also the lengths "before" and "after" the intersection point in respect of the first lever 12.

Figure 3:
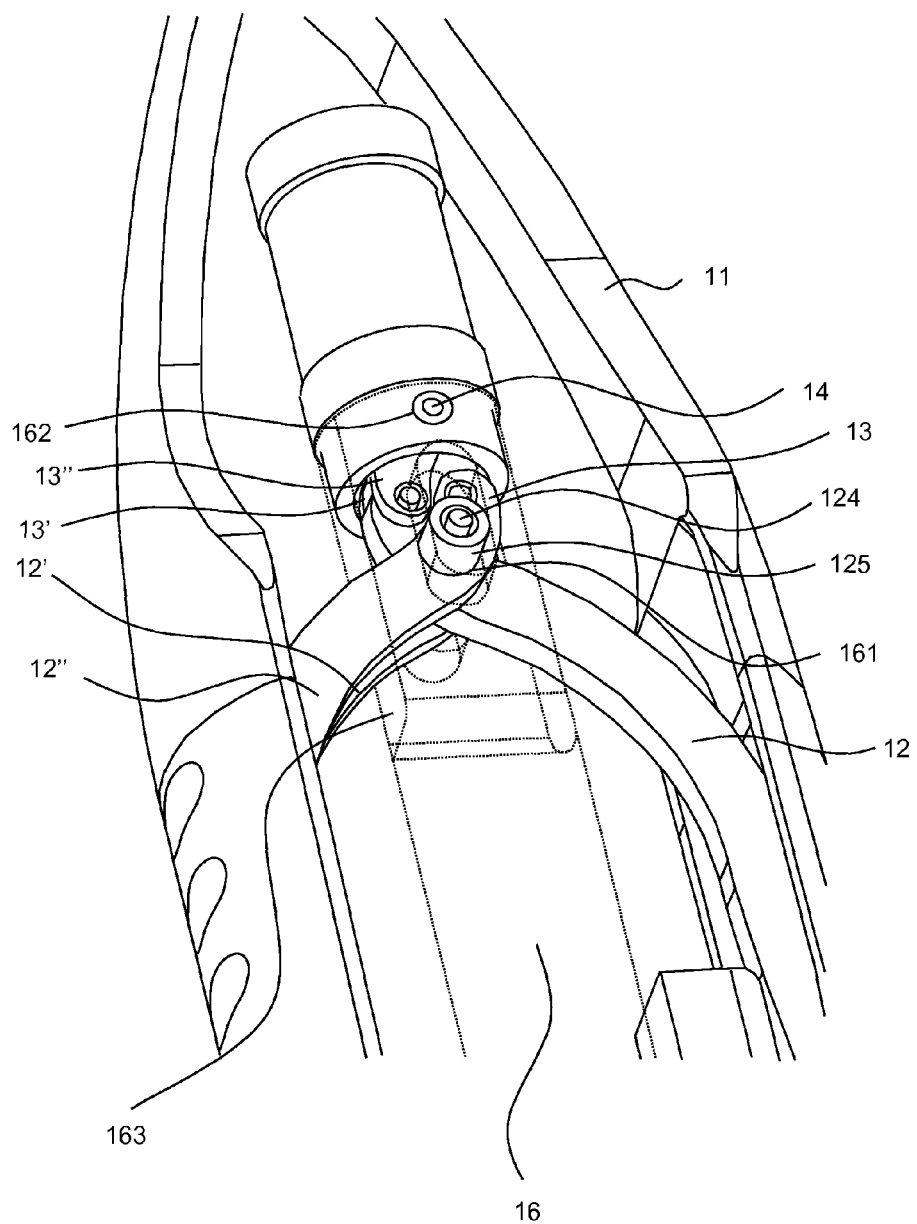
FIG. 3 shows a perspective view of the grip parts, of the first and second levers and of the inner shank of an actuation grip.

The axial pin 124 is furthermore guided through the through-bores 126 such that it protrudes on both sides from the first levers 12, wherein guide rollers 125 are mounted on the respective ends of the axial pin 124, and wherein the guide rollers 125 run in oblong holes 161, which are present in the inner shank 16 (see FIG. 3 in this connection). The inner shank 16 is axially movable with respect to the outer shank 15. The guide pin is secured in the inner shank, as a result of which a pivoting movement of the grip parts 11 can be converted to an axial movement of the shank 16 relative to the shank 15.

If the grip parts 11 are now pressed together, this pivoting movement is first of all transmitted to the first levers 12, which in turn transmit the movement to the double scissor hinge. In this process, the inner shank 16 with the oblong holes 161 moves relative to the axial pin 124 in such a way that, in relation to the oblong holes 161, the axial pin 124 appears to move to a proximal end of these oblong holes 161. Since the axial pin 124 is guided in the oblong holes 161, it can move exclusively in the longitudinal direction of the shank. The movement of the first levers 12 naturally also causes a movement of the second levers 13 and leads to an axial movement of the inner shank 16 toward the proximal end of the actuation grip 1.

The figures do not show that the double scissor hinge can in principle also be secured on the shanks 15, 16 in such a way that, when the grip parts 11 are actuated, the inner shank 16 can move toward the distal end 1", which is necessary for actuation of pressure-actuated surgical tools.

A quick-change device 18 for a microsurgical instrument can also be seen in FIG. 1, located at the distal end 1" of the actuation grip 1. Microsurgical instruments can be quickly and easily docked and undocked on this quick-change device 18. In addition, a locking device 17 is also shown, by means of which the grip parts 11 can be locked in a closed position, i.e. in a position in which the microsurgical instrument would be "closed". The locking device 17 is here designed in two parts and has a prong assigned to the grip part 11 and a corresponding clip assigned to the outer shank.

On its part assigned to the outer shank, the locking device can also have a slide with which it can be activated, but this is not shown in the figures.

Figure 2:
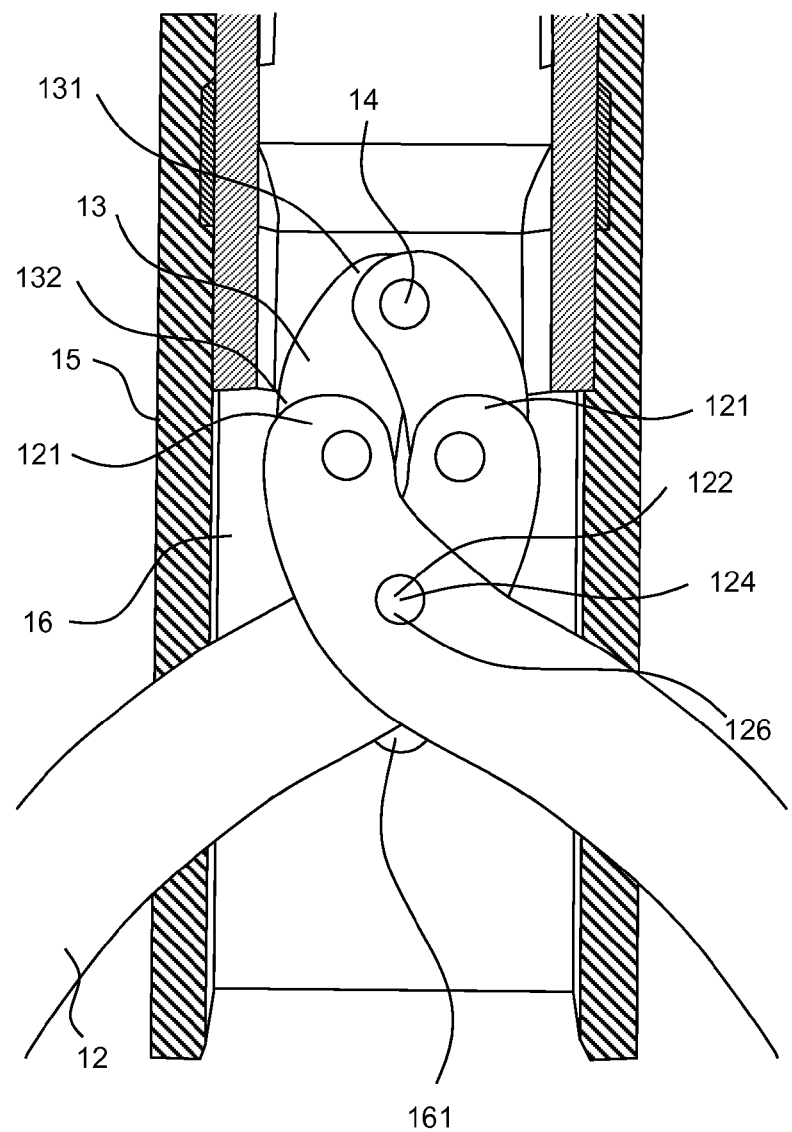
FIG. 2 shows a longitudinal section through an area of an actuation grip with a double scissor hinge.

The area located around the scissor hinge in FIG. 1 is shown in more detail in FIG. 2, in which the first levers 12 are in an actuated state, as is illustrated by the fact that the angle which they enclose with the outer shank 15 is much smaller than in FIG. 1. The pivoting movement executed by the grip parts 11 (see FIG. 1) upon actuation is transmitted to the first levers 12, which perform a rotation about the intersection point 122 and in turn transmit the movement to the second levers 13, wherein the double scissor hinge, formed by the first levers 12 and the second levers 13, narrows and thereby lengthens. Since the axial pin 124 that rotatably couples the first levers 12 is guided in the oblong holes 161, and since the guide pin 14 that rotatably couples the second levers 13 to each other is secured in the inner shank 16, the lengthening performed by the scissor hinge is transmitted as an axial movement to the inner shank 16. In this process, the axial pin 124 is guided in the oblong holes 161 present in the inner shank 16, which prevents a situation where actuation causes the first levers to tilt.

It will also be seen from FIG. 3 that one of the first levers 12 and one of the second levers 13 is designed in two parts. A first lever 12 is here composed of two identical lever halves 12', 12" which are arranged in parallel and are spaced apart along the axial pin 124 that connects the first levers 12. At the intersection point 122, the two-part first lever 12 receives the other first lever 12, which is in one part, wherein the axial pin 124 is inserted through the three lever halves that lie over one another there. At its end 131 (see FIG. 2) directed away from the grip part, the two-part first lever 12 receives, between its lever halves 12', 12", a one-part second lever 13, whereas the one-part first lever 12 is received by a similarly two-part second lever 13, which is composed of two identical lever halves 13', 13". The axial pin guided through the first levers 12 is inserted right through the first levers 12 to such an extent that it is guided on oblong holes 161 present in the inner shank 16, such that the first levers 12 have little play not in a direction that does not correspond to the main direction of movement for the actuation.

On both ends of the axial pin 124, guide rollers 125 are mounted that roll in the oblong hole 161, in order in this way to reduce the actuation forces in relation to a sliding movement and to further reduce the play that occurs, which can be of particularly small dimension through the use of rollers mounted on rolling bearings.

In the inner shank 16, a recess 162 can also be seen through which is inserted the guide pin 14, which connects the second levers 13 in an articulated manner at their ends 131 (see FIG. 2) directed away from the first levers. In this area, the inner shank 16 is a circular hollow cylinder, wherein the recess 162 is thus present on respectively opposite parts of the lateral face of the hollow cylinder. The first levers 12 are additionally guided in an insert slit 163 that extends along a longitudinal axis in the inner shank 16. It can be clearly seen that the double scissor hinge formed by the first levers 12 and second levers 13 is well protected by the insert slit 163 and by the hollow cylindrical portion of the inner shank 16, as a result of which the mechanism is protected from contamination and there is no danger of its becoming jammed on external devices, as is the case with a mechanism arranged on the outside.

LIST OF REFERENCE SIGNS 1 actuation grip
1' proximal end of the actuation grip
1" distal end of the actuation grip
11 grip part
111 proximal end of the grip part
112 distal end of the grip part
113 attachment point of the first lever on the grip part
12 first lever
12' first lever half of the first lever
12" second lever half of the first lever
121 end of the first lever directed away from the grip part
122 intersection point of the first levers
123 end of the first lever directed toward the grip part
124 axial pin
125 guide roller
126 bore at the intersection point
13 second lever
13' first lever half of the second lever
13" second lever half of the second lever
131 end of the second lever directed away from the first lever
132 end of the second lever directed toward the first lever
14 guide pin
15 outer shank
16 inner shank
161 oblong hole in the inner shank
162 recess of the inner shank for receiving the guide pin
163 insert opening of the inner shank for first levers
17 locking device
18 quick-change device

The invention claimed is:

1. An actuation grip for a microsurgical instrument, comprising:
an inner shaft surrounded coaxially and cylindrically by an outer shaft, wherein the inner shaft and the outer shaft are axially movable relative to each other;
two grip parts, each with two ends, coupled pivotably at a proximal end of the actuation grip, wherein:
each of the two grip parts includes a first lever articulated rotatably via an attachment point between the two ends of the respective grip part, and
the respective first levers of the two grip parts have, in each case at an intersection point between their respective ends, a bore in which an axial pin is arranged that couples the first levers rotatably to each other, and
the first levers, at their respective ends directed away from the grip parts, are each connected rotatably to one or more second levers, such that the first levers form, with the one or more second levers, a double scissor hinge, and
the one or more second levers, at their respective ends directed away from the first levers, are mounted rotatably on a common guide pin, which is secured in opposite recesses of at least one of a shaft wall of the inner shaft and a shaft wall of the outer shaft;
wherein the one or more second levers of the double scissor hinge are present entirely within an outer contour of the inner shaft.

2. The actuation grip according to claim 1, wherein the guide pin is secured in opposite recesses of the shaft wall of the inner shaft.

3. The actuation grip according to claim 1, wherein the axial pin
extends, at the intersection point, with both ends beyond the respective bores of the first levers, and is guided at both ends in a respective oblong hole of the inner shaft, via guide rollers which are arranged on ends of the axial pin and which are designed to roll in the oblong hole.

4. The actuation grip according to claim 3, wherein, on a circumference of the inner shaft on which the oblong hole is also present, the inner shaft has, offset by 90° with respect to the oblong hole, an insert slit for the first levers.

5. The actuation grip according to claim 1, wherein, at a distal end of the actuation grip, there is a change-over device for a microsurgical instrument.

6. The actuation grip according to claim 1, wherein
one of the first levers includes two identical first lever halves which are arranged in parallel and are spaced apart from each other along the axial pin and between which the other first lever is received, and
the one of the first levers is received by one of the one or more second levers, which is composed of two identical second lever halves which are arranged in parallel and are spaced apart from each other along the axial pin.

7. The actuation grip according to claim 1, wherein the first levers are longer than each of the one or more second levers, wherein a length ratio of the first levers to the one or more second levers lies in a range between 1:15 and 1:3.

8. The actuation grip according to claim 7, wherein the length ratio of the first levers to the one or more second levers lies in a range between 1:12 and 1:16.

9. The actuation grip according to claim 1, wherein at least one of the two grip parts can be locked, by a locking device, in a predetermined angle position with respect to a longitudinal axis of the inner shaft and the outer shaft.

10. The actuation grip according to claim 1, wherein an axial spring element is arranged in one of the inner shaft and the outer shaft in order to transmit force to the respective other shaft.

11. A microsurgical instrument for minimally invasive surgery, comprising:
at least one hollow shaft and with an actuation device movable axially thereto;
an actuation grip at a proximal end of the microsurgical instrument, the actuation grip coupled to the actuation device by a change-over device;
a surgical tool at a distal end of the microsurgical instrument, which can be actuated by the actuation device;
wherein the actuation grip includes:
an inner shaft surrounded coaxially and cylindrically by an outer shaft, wherein the inner shaft and the outer shaft are axially movable relative to each other:
two grip parts, each with two ends, coupled pivotably at a proximal end of the actuation grip, wherein:
each of the two grip parts includes a first lever articulated rotatably via an attachment point between the two ends of the respective grip part and
the respective first levers of the two grip parts have, in each case at an intersection point between their respective ends, a bore in which an axial pin is arranged that couples the first levers rotatably to each other, and
the first levers, at their respective ends directed away from the grip parts, are each connected rotatably to one or more second levers, such that the first levers form with the one or more second levers a double scissor hinge and
the one or more second levers, at their respective ends directed away from the first levers, are mounted rotatably on a common guide pin which is secured in opposite recesses of at least one of a shaft wall of the inner shaft and a shaft wall of the outer shaft;
wherein the one or more second levers of the double scissor hinge are present entirely within an outer contour of the inner shaft.

12. The microsurgical instrument according to claim 11, wherein
the surgical tool is in the form of at least one of scissors, forceps, a gripper, and a pincer; and/or
the change-over device is a quick-change device.

13. An actuation grip for a microsurgical instrument, comprising:
an inner shaft surrounded coaxially and cylindrically by an outer shaft, wherein the inner shaft and the outer shaft are axially movable relative to each other;
two grip parts, each with two ends, coupled pivotably at a proximal end of the actuation grip, wherein:
each of the two grip parts includes a first lever articulated rotatably via an attachment point between the two ends of the respective grip part, and
the respective first levers of the two grip parts have, in each case at an intersection point between their respective ends, a bore in which an axial pin is arranged that couples the first levers rotatably to each other, and
the first levers, at their respective ends directed away from the grip parts, are each connected rotatably to one or more second levers, such that the first levers form, with the one or more second levers, a double scissor hinge, and
the one or more second levers, at their respective ends directed away from the first levers, are mounted rotatably on a common guide pin, which is secured in opposite recesses of at least one of a shaft wall of the inner shaft and a shaft wall of the outer shaft;
wherein the axial pin
extends, at the intersection point, with both ends beyond the respective bores of the first levers, and
is guided at both ends in a respective oblong hole of the inner shaft, via guide rollers which are arranged on ends of the axial pin and which are designed to roll in the oblong hole.

14. The actuation grip according to claim 13, wherein the guide pin is secured in opposite recesses of the shaft wall of the inner shaft.

15. The actuation grip according to claim 13, wherein, on a circumference of the inner shaft on which the oblong hole is also present, the inner shaft has, offset by 90° with respect to the oblong hole, an insert slit for the first levers.

16. The actuation grip according to claim 13, wherein
one of the first levers includes two identical first lever halves which are arranged in parallel and are spaced apart from each other along the axial pin and between which the other first lever is received, and
the one of the first levers is received by one of the one or more second levers, which is composed of two identical second lever halves which are arranged in parallel and are spaced apart from each other along the axial pin.

17. The actuation grip according to claim 13, wherein the first levers are longer than each of the one or more second levers, wherein a length ratio of the first levers to the one or more second levers lies in a range between at least one of 1:15 and 1:3.

18. The actuation grip according to claim 13, wherein at least one of the two grip parts can be locked, by a locking device, in a predetermined angle position with respect to a longitudinal axis of the inner shaft and the outer shaft.

19. The actuation grip according to claim 13, wherein an axial spring element is arranged in one of the inner shaft and the outer shaft in order to transmit force to the respective other shaft.

20. The actuation grip according to claim 13, wherein the one or more second levers of the double scissor hinge are present entirely within an outer contour of the inner shaft.

* * * * *